(12) United States Patent
Miller et al.

(10) Patent No.: US 7,404,818 B2
(45) Date of Patent: Jul. 29, 2008

(54) SIDE-LOADING ADJUSTABLE BONE ANCHOR

(75) Inventors: Keith E. Miller, Memphis, TN (US); Greg Denzer, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 327 days.

(21) Appl. No.: 11/000,585

(22) Filed: Nov. 30, 2004

(65) Prior Publication Data

US 2006/0116687 A1 Jun. 1, 2006

(51) Int. Cl.
*A61B 17/56* (2006.01)
(52) U.S. Cl. .......................................... 606/73; 606/61
(58) Field of Classification Search .................. 606/61, 606/62, 73
See application file for complete search history.

(56) References Cited

U.S. PATENT DOCUMENTS

| | | |
|---|---|---|
| 4,641,636 A | 2/1987 | Cotrel |
| 4,815,413 A | 3/1989 | Kota |
| 5,005,562 A | 4/1991 | Cotrel |
| 5,067,955 A | 11/1991 | Cotrel |
| 5,487,742 A | 1/1996 | Cotrel |
| 5,534,001 A * | 7/1996 | Schlapfer et al. ............... 606/61 |
| 5,578,033 A | 11/1996 | Errico et al. |
| 5,584,834 A | 12/1996 | Errico et al. |
| 5,601,552 A | 2/1997 | Cotrel |
| 5,603,714 A | 2/1997 | Kaneda et al. |
| 5,603,885 A | 2/1997 | McGinty |
| 5,669,911 A | 9/1997 | Errico et al. |
| 5,690,630 A | 11/1997 | Errico et al. |
| 5,733,285 A | 3/1998 | Errico et al. |
| 5,797,911 A | 8/1998 | Sherman et al. |
| 5,809,594 A | 9/1998 | Isogai |
| 5,817,094 A | 10/1998 | Errico et al. |
| 5,885,286 A | 3/1999 | Sherman et al. |
| 5,989,250 A | 11/1999 | Wagner et al. |
| 6,132,430 A | 10/2000 | Wagner |
| 6,280,442 B1 | 8/2001 | Barker et al. |
| 6,416,515 B1 | 7/2002 | Wagner |

(Continued)

FOREIGN PATENT DOCUMENTS

EP 1 064 885 1/2001

OTHER PUBLICATIONS

Medtronic Sofamor Danek, Inc.; "Medtronic Sofamor Danek Product Catalog": pp. A-38, A-39; 2000.

*Primary Examiner*—Eduardo C Robert
*Assistant Examiner*—Tara George
(74) *Attorney, Agent, or Firm*—Woodard, Emhardt, Moriarty, McNett & Henry LLP

(57) ABSTRACT

A side-loading bone anchor is provided, which may be used in cervical, thoracic, lumbar or sacral areas of the spine or other orthopedic locations. In one embodiment, the anchor includes an anchoring portion, a receiving portion, and an internal piece that is rotatable with respect to the receiving portion at least to a degree. The anchoring portion is attached to a bone. A rod or other elongated support member is received in the receiving portion in contact with the internal piece. The rod and internal piece may be rotated for variability substantially in a plane, and a set screw is threaded into the receiving portion to lock the rod within the receiving portion.

34 Claims, 5 Drawing Sheets

U.S. PATENT DOCUMENTS

| | | |
|---|---|---|
| 6,471,705 B1 * | 10/2002 | Biedermann et al. .......... 606/61 |
| 6,485,491 B1 | 11/2002 | Farris et al. |
| 6,520,963 B1 * | 2/2003 | McKinley .................... 606/61 |
| 6,547,789 B1 | 4/2003 | Ventre et al. |
| 6,562,040 B1 | 5/2003 | Wagner |
| 6,613,050 B1 * | 9/2003 | Wagner et al. ................ 606/61 |
| 2002/0091386 A1 * | 7/2002 | Martin et al. ................. 606/61 |
| 2003/0199873 A1 * | 10/2003 | Richelsoph .................. 606/61 |

* cited by examiner

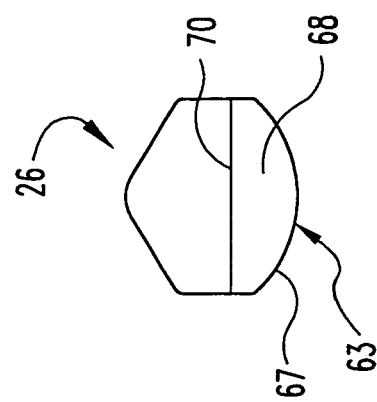
Fig. 13
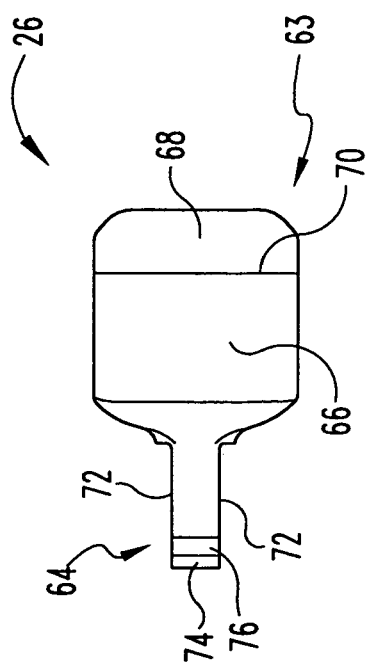
Fig. 10
Fig. 11
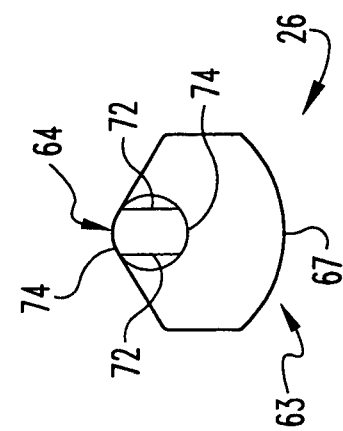
Fig. 12

SIDE-LOADING ADJUSTABLE BONE ANCHOR

BACKGROUND OF THE INVENTION

The present invention concerns bone anchors, particularly useful for engagement in the vertebrae. In a particular embodiment, the invention contemplates a bone screw assembly that allows loading of an elongated rod or other member extending along the spine from the side, while enabling adjustment of the rod substantially in a plane.

Several techniques and systems have been developed for correcting and stabilizing the spine and for facilitating fusion at various levels of the spine. In one type of system, a bendable rod is disposed longitudinally along the length of the spine or vertebral column. The rod may be preferably bent to correspond to the normal curvature of the spine in the particular region being instrumented. For example, the rod can be bent to form a normal kyphotic curvature for the thoracic region of the spine, or a lordotic curvature for the lumbar region. In accordance with such a system, the rod is engaged to various vertebrae along the length of the spinal column by way of a number of fixation elements. A variety of fixation elements can be provided which are configured to engage specific portions of the vertebra. For instance, one such fixation element is a hook that is configured to engage the laminae of the vertebra. Another very prevalent fixation element is a spinal screw which can be threaded into various aspects of the vertebral bone.

In one typical procedure utilizing a bendable rod, the rod is situated on one or opposite sides of the spine or spinous processes. A plurality of bone screws are threaded into a portion of several vertebral bodies, for example into the pedicles of these vertebrae. The rod(s) are connected or affixed to these plurality of bone screws to apply corrective and stabilizing forces to the spine.

One example of a rod-type spinal fixation system is the TSRH® Spinal System sold by Medtronic Sofamor Danek, Inc. The TSRH® System includes elongated rods and a variety of hooks, screws and bolts all configured to create a segmental construct throughout the spine. In one aspect of the TSRH® System, the spinal rod is connected to the various vertebral fixation elements by way of an eyebolt. In this configuration, the fixation elements are engaged to the spinal rod laterally adjacent to the rod. In another aspect of the TSRH® System, a variable angle screw is engaged to the spinal rod by way of an eyebolt. The variable angle screw allows pivoting of the bone screw in a single plane that is parallel to the plane of the spinal rod. Details of this variable angle screw can be found in U.S. Pat. No. 5,261,909 to Sutterlin et al., owned by the Assignee of the present invention. One goal achieved by the TSRH® System is that the surgeon can apply vertebral fixation elements, such as a spinal hook or a bone screw, to the spine in appropriate anatomic positions. The TSRH® System also allows the surgeon to easily engage a bent spinal rod to each of the fixation elements for final tightening.

Another rod-type fixation system is the Cotrel-Dubosset/CD Spinal System sold by Medtronic Sofamor Danek, Inc. Like the TSRH® System, the CD® System provides a variety of fixation elements for engagement between an elongated rod and the spine. In one aspect of the CD® System, the fixation elements themselves include a body that defines a slot within which the spinal rod is received. The slot includes a threaded bore into which a threaded plug is engaged to clamp the rod within the body of the fixation element. The CD® System includes hooks and bone screws with this "open-back" configuration. Details of this technology can be found in U.S. Pat. No. 5,005,562 to Cotrel. One benefit of this feature of the CD® System is that the fixation element is positioned directly beneath the elongated rod. This helps reduce the overall bulkiness of the implant construct and minimizes the trauma to surrounding tissue.

These and other vertebral anchors have channels for an elongated rod or other member that open upward, i.e. directly away from the bone to which the anchor is attached. The convenience of such a structure is clear, as the anchor can be first placed in the bone, then the rod can be essentially lain on top of it, within the channel. In many cases, however, a surgeon may wish to use anchors to translate the vertebral body to the rod. This translation will typically involve horizontal as well as vertical components. Side loading implants, along with their associated instruments, can simplify the execution of this type of maneuver. Use of such implants can present less interference from lateral tissue, the potential to pre-load the locking components prior to inserting the anchor and also innovative means of provisionally capturing the rod prior to final tightening.

To address these issues, bone anchors having a channel opening to the side have been developed. However, new and improved side-loading bone anchors are still needed in the industry.

BRIEF DESCRIPTION OF THE FIGURES

FIG. 10 is a top view of an embodiment of an internal piece useable in the apparatus shown in FIG. 1.

FIG. 11 is a side view of the embodiment shown in FIG. 10.

FIG. 12 is a rear view of the embodiment shown in FIG. 10.

FIG. 13 is a front view of the embodiment shown in FIG. 10.

DESCRIPTION OF A PREFERRED EMBODIMENT

Figure 1:
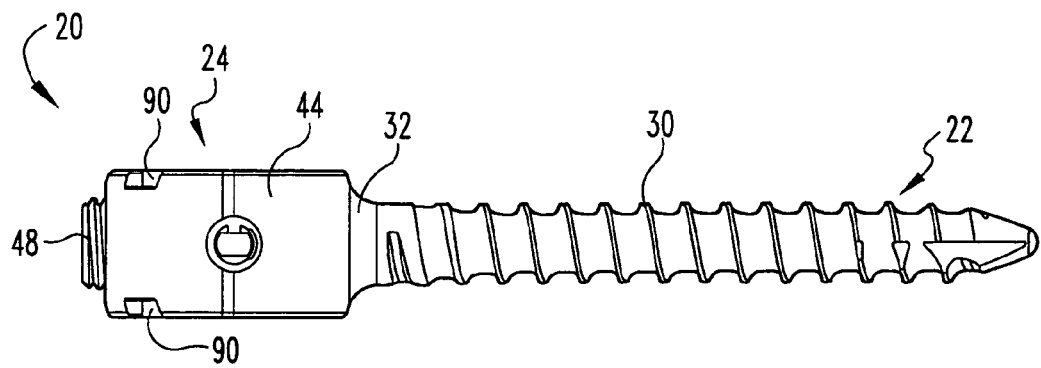
FIG. 1 is a side view of an embodiment of a side-loading sagitally-adjustable bone anchor.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Looking first at FIGS. 1-4, there is shown an embodiment of a side-loading bone screw 20. Bone screw 20 may be made for attachment to vertebrae, such as cervical, thoracic, lumbar and or sacral bone structures, or other bones or tissues. Similarly, aspects of bone screw 20 described herein can be included in vertebral hooks, bone clamps, and other orthopedic implant devices.

Screw 20, in the embodiment shown in FIG. 1, includes a shaft 22, a receiving portion 24, and an internal piece 26. Shaft 22 is an elongated piece having one or more threads 30 on at least a portion, e.g. a relatively lower portion. Thread 30 may be a cancellous thread, of a configuration suited to implantation into a vertebra or similar bone. Thread 30 may be self-tapping or intermittent, or may have more than one crest winding about shaft 22, or of other appropriate configurations. A neck 32 at a relatively upper portion of shaft 22 is provided. Neck 32 may be above thread 30, or may also include thread(s) or a threaded portion. In an embodiment in which shaft 22 is integrally joined to receiving portion 24, as by unitary formation or construction or by solid attachment, neck 32 is attached to receiving portion 24.

Referring now additionally to FIGS. 5-9, the depicted embodiment of receiving portion 24 is substantially C-shaped, having an upper leg 40, a lower leg 42, and an intermediate portion 44 joining them. Upper leg 40 has a threaded aperture 46 into which a set screw 48 can be threaded. Aperture 46 may have a longitudinal axis that is perpendicular to upper leg 40, or such axis may be angled with respect to upper leg 40, e.g. toward intermediate portion 44.

Figure 2:
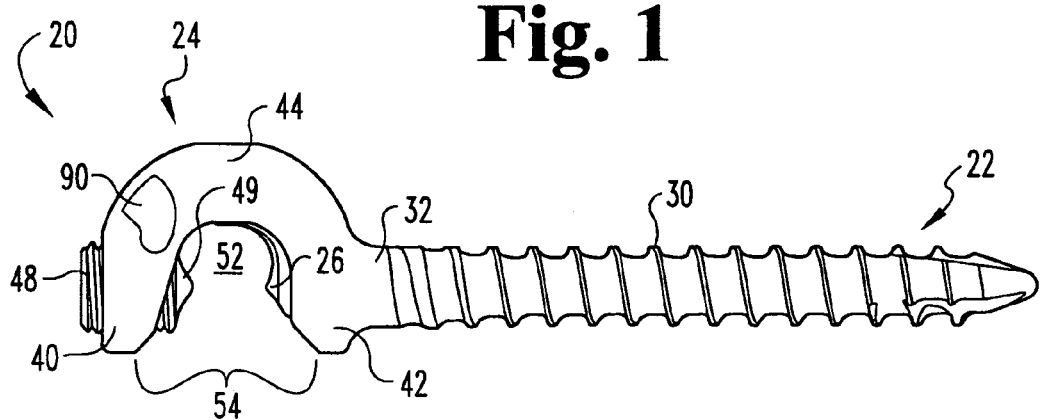
FIG. 2 is a side view of the embodiment shown in FIG. 1, rotated ninety degrees with respect to FIG. 1.
Figure 3:
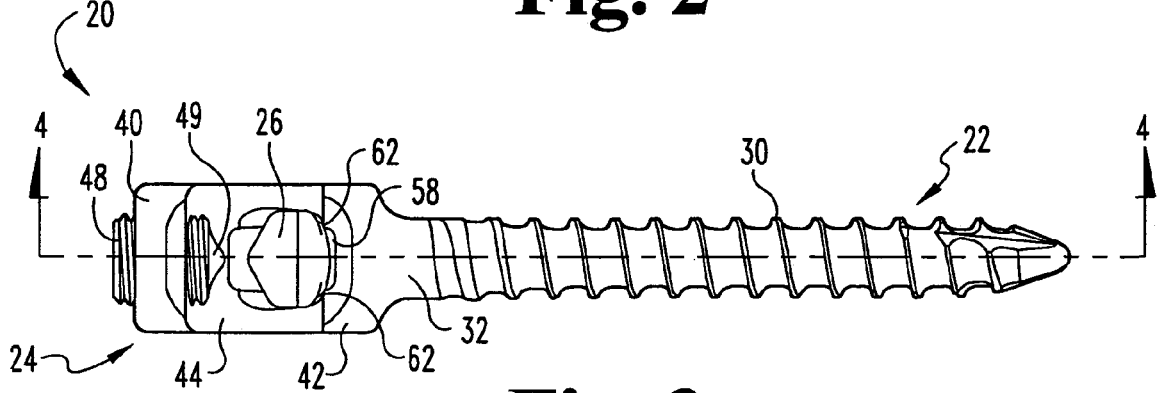
FIG. 3 is a side view of the embodiment shown in FIG. 1, rotated 180 degrees with respect to FIG. 1.
Figure 4:
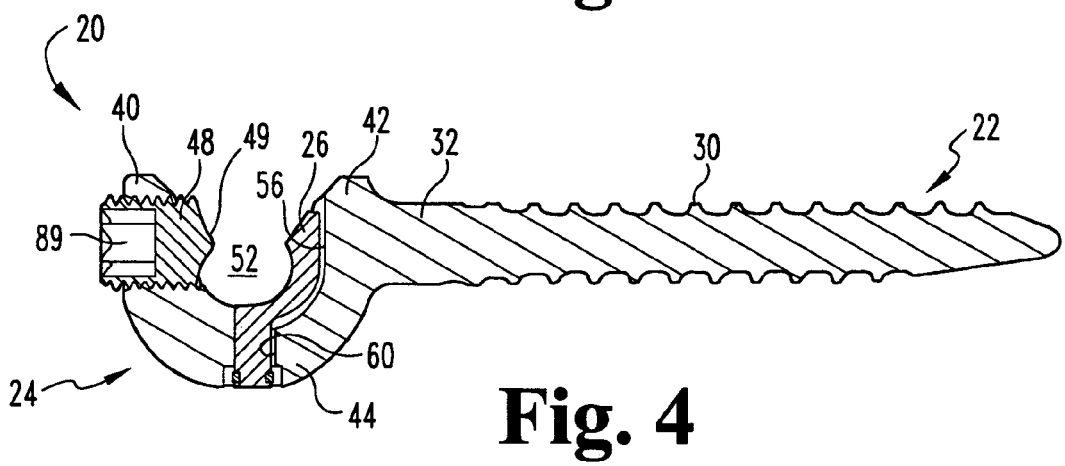
FIG. 4 is cross-sectional view of the embodiment shown in FIG. 1, taken along the lines 4-4 in FIG. 3 and viewed in the direction of the arrows.
Figure 5:
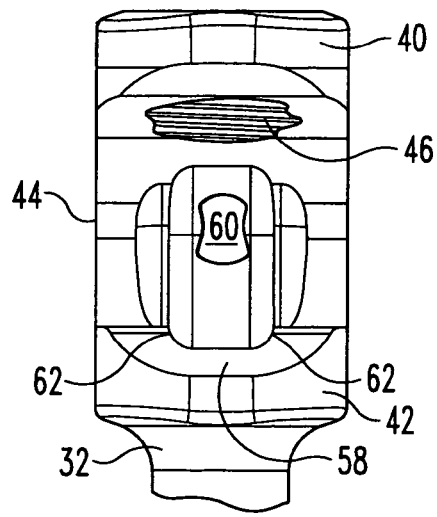
FIG. 5 is a side view of a portion of the embodiment shown in FIG. 1.

Lower leg 42 may connect to shaft 22. As previously noted, in one embodiment shaft 22 is integrally joined to receiving portion 24. As shown in FIGS. 2 and 4, shaft 22 may be attached in a particular embodiment to receiving portion 24 at a relatively forward portion of lower leg 42. Shaft 22 may also be attached to receiving portion 24 at other parts of receiving portion 24. As one example, shaft 22 could be attached at a central portion of leg 42, i.e. an area approximately equidistant from intermediate portion 44 and a front or opening portion of receiving portion 24. Shaft 22 could also be attached to leg 42 at a rearward portion, i.e. an area relatively close to or at intermediate portion 44.

Figure 6:
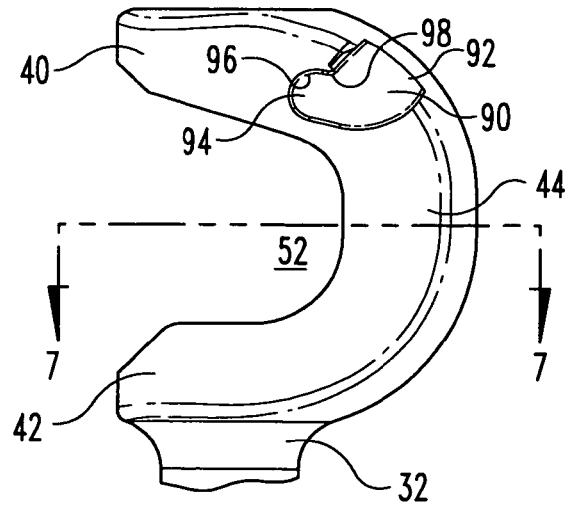
FIG. 6 is a side view of the portion shown in FIG. 5, rotated ninety degrees with respect to FIG. 5.
Figure 7:
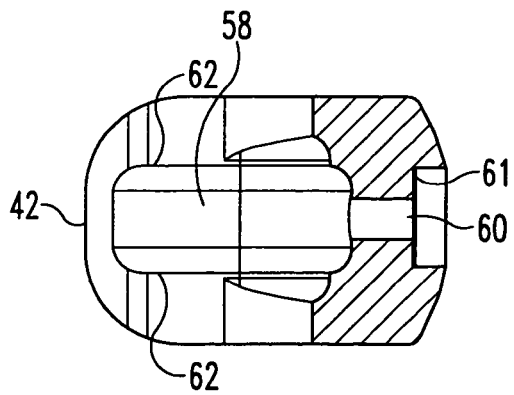
FIG. 7 is a cross-sectional view taken along the lines 7-7 in FIG. 6 and viewed in the direction of the arrows.
Figure 9:
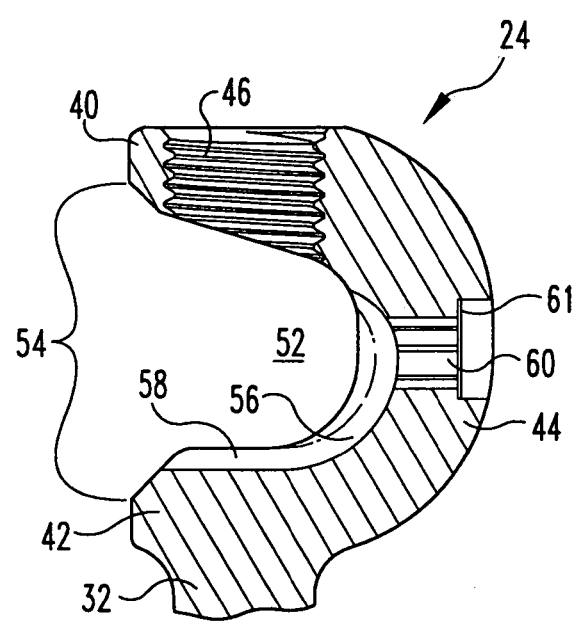
FIG. 9 is a cross-sectional view taken along the lines 9-9 in FIG. 8 and viewed in the direction of the arrows.
Figure 8:
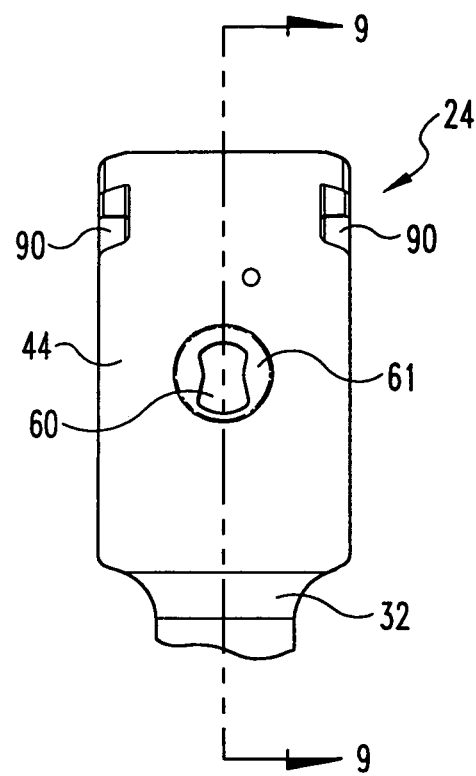
FIG. 8 is a side view of the portion shown in FIG. 5, rotated 180 degrees with respect to FIG. 5.
Figure 14:
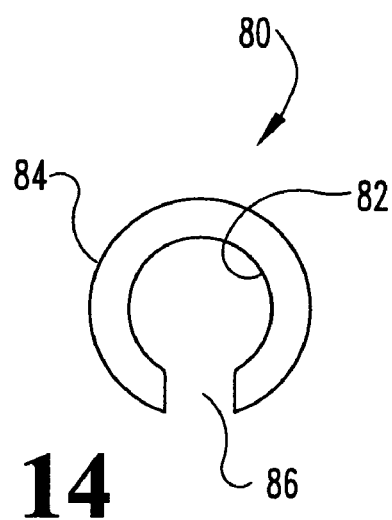
FIG. 14 is a top view of an embodiment of a clip useable in the apparatus shown in FIG. 1.
Figure 16:
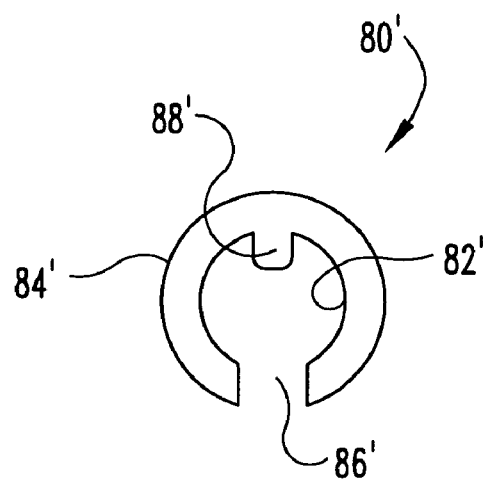
FIG. 16 is a top view of another embodiment of a clip useable in the apparatus shown in FIG. 1.
Figure 15:
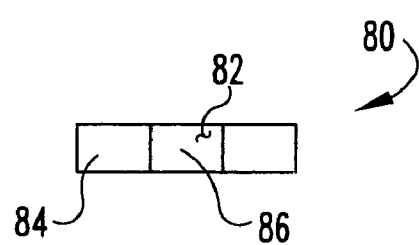
FIG. 15 is a side view of the embodiment shown in FIG. 14.

Intermediate portion 44 joins legs 40 and 42. Taken together, legs 40 and 42 and intermediate portion 44 form substantially a C-shape, with a channel 52 substantially to one side of intermediate portion 44 and having a mouth 54 between legs 40 and 42. In a particular embodiment, mouth 54 is somewhat wider than the breadth of channel 52 further within receiving portion 24. For example, as shown in FIGS. 2 and 6, channel 52 may taper substantially uniformly from mouth 54 toward intermediate portion 44.

The illustrated embodiment of receiving portion 24 further includes a cavity 56 in lower leg 42 and intermediate portion 44. Cavity 56 is relatively shallow in an area or hollow 58 substantially corresponding to lower leg 42. Cavity 56 may be substantially cylindrical and relatively deep in an area or hole 60 into or through intermediate portion 44. Alternatively, at least a part of cavity 56 in the area 60 in intermediate portion 44 may have a substantially hour-glass shape (e.g. somewhat wider at upper and lower ends than at an area between the upper and lower ends). A rim or flange 61 extends at least partially around area 60 of cavity 56 in a position relatively distant from channel 52 to assist in retaining internal piece 26, as will be described further below. Rim or flange 61 may extend around substantially the entire circumference of area 60 of cavity 56, or may extend around somewhat less than that circumference.

In the area of or adjacent to cavity 56, in a particular embodiment receiving portion 24 is provided with one or more ridges 62. Ridges 62 are provided to engage the underside of internal piece 26 when screw 20 is locked. In the illustrated embodiment, ridges 62 are positioned substantially perpendicular to the direction of a rod in channel 52. It will be seen that ridges 62 could be positioned substantially parallel or obliquely to such a rod, could be positioned substantially in a chevron-type formation, or in any other way to help lock internal piece 26 and receiving portion 24 against movement with respect to each other. Alternatively, splines or other engaging structure can be provided on both the internal piece 26 (e.g. on its external surface 67) and on the receiving portion 24 in the area 58 of cavity 56.

Internal piece 26 includes a rounded seat portion 63 and a post portion 64. Seat portion 63 has an internal curved surface 66, an external curved surface 67, and a substantially flat front surface 68. Internal surface 66, in a particular embodiment, has a substantially cylindrical shape which can have a radius the same as or similar to that of a rod to be used with screw 20. Internal surface 66 and front surface 68 may come together in an edge 70. In a particular embodiment, the total arc of internal surface 66, from post portion 64 to edge 70, is less than 180 degrees, and may be about 120 degrees. It will be seen that other embodiments of internal piece 26 may have an internal surface including an arc equal to or somewhat greater than 180 degrees. In such a case, a rod having substantially the same diameter as such an internal surface may form a snap-fit or interference fit with such internal surface. A rod of substantially smaller diameter than such an internal surface would, of course, fit without interference.

Post portion 64 extends from one end of seat portion 63. In the illustrated embodiment, post portion 64 and seat portion 63 are substantially in the same plane. Post portion 64 is substantially rectangular in cross-section, with two substantially smooth flat side surfaces 72 and substantially smooth curved top and bottom surfaces 74. A groove 76 is provided in at least one of the surfaces 72 or 74 of post portion 64, and in a particular embodiment a plane including groove 76 is substantially perpendicular to post portion 64.

Internal piece 26 is inserted into cavity 56 of receiving portion 24 so that post portion 64 is within area 60 of cavity 56, and seat portion 63 is at least partially within area 58 of cavity 56. When this insertion is complete, internal piece 26 can rotate with respect to receiving portion 24 about post portion 64. Seat portion 63 generally rotates in a plane that is dictated by the placement of screw 20. For example, if screw 20 is attached to a vertebra, internal piece 26 can rotate so that seat portion is in a generally sagittal plane. As another example, if screw 20 is used with a lateral connector, such that screw 20 is about 90 degrees left or right from a rod or vertebral column, internal piece 26 can rotate so that seat portion is in a generally coronal plane. In an embodiment in which area 58 of cavity 56 is substantially cylindrical, internal piece 26 may rotate in a complete circle with respect to receiving portion 24, unless seat portion 63 interferes with upper leg 40 or another part of receiving portion 24. In an embodiment in which area 58 of cavity 56 is of an hour-glass shape, the possible amount of rotation of internal piece 26 with respect to receiving portion 24 is limited, as the sides of the hour-glass portion of cavity 56 will engage one or both of surfaces 72 after internal piece 26 and receiving portion 24 are rotated with respect to each other through a certain angle. Curved surfaces 74 of post portion 64 do not interfere with similarly curved boundaries of hour-glass portion of cavity 56.

To retain internal piece 26 within receiving portion 24 while allowing the relative rotation previously described prior to placement of a rod in receiving portion 24 adjacent internal piece 26, and locking of screw 20 to such a rod, a ring clip 80 may be provided. Clip 80 is a substantially circular C-shaped member with an inner diameter 82, an outer diameter 84, and a gap 86. In another embodiment, a similar clip 80' with a gap 86' may include an internal extension part 88'. Clip 80 may be elastically deformable by widening or narrowing gap 86 to a degree greater than exists in the normal, unstressed state of clip 80. When internal piece 26 is inserted into receiving portion 24, clip 80 is placed around post portion 64 of internal piece 26. In one embodiment, clip 80 is placed so that at least a part of clip 80, e.g. inner diameter 82 and possibly more, within groove 76 of post portion 64. Clip 80' could be placed so that at least a portion, e.g. some or all of extension part 88', is within groove 76. When clip 80 is around post portion 64, post portion 64 cannot be withdrawn from cavity 56 of receiving portion 24 due to interference between clip 80 and rim or flange 61. Clip 80 does not interfere with rotational movement of internal piece 26 with respect to receiving portion 24. Alternatively, other methods of retaining internal piece 26 in receiving portion 24 can be used, such as peening post portion 62 within cavity 56. As with clip 80, it is preferable but not necessary with such alternative methods that internal piece 26 be capable of rotation with respect to receiving portion 24 prior to final locking of screw 20.

Set screw 48 includes external threads adapted for engagement with threaded aperture 46. In one embodiment, set screw 48 includes an imprint 89 in or on a top surface adapted for engagement with a tool for tightening and/or loosening set screw 48. Imprint 89 may be internal, e.g. a hexagonal or hexalobed opening, or may be external, e.g. a hexagonal head. It will be seen that an internal print may be preferred as it may add nothing or a smaller amount to the overall height or profile of screw 20. Set screw 48 may further include a curved, pointed, conical or other surface 49 at the bottom. Such a surface engages a rod within receiving portion 24 as further described below. Set screw 48 may be placed at least partially within threaded aperture 46 such that none or a very small amount of set screw 48 extends into channel 52. Alternatively, set screw may be left out of aperture 46 until a rod is inserted into receiving portion 24, and may then be inserted into aperture 46 and against the rod, as is further described below.

In addition to the features of the embodiment described above, receiving portion 24 may further include one or more indentations 90 for receiving a gripping or positioning tool. Indentations 90 are shown in one embodiment on either side of receiving portion 24, in an area in or adjacent to upper leg 40 and intermediate portion 44. It will be seen that indentations 90 could be in any part of receiving portion 24. Indentations 90 in the illustrated embodiment have an entry portion 92 and a holding portion 94. Holding portion 94 has a rounded or part circular portion 96 having a corner 98. A holding or gripping tool (not shown) having one or more rounded or circular protrusions at or adjacent to the end(s) of such a tool may be used. Such protrusion(s) may be inserted at entry portion(s) 92 and curved, angled or hooked around corner 98 into circular portion 96. In this manner, such a tool can be used to hold, position, manipulate or otherwise work on or with screw 20.

In use, a surgeon first prepares the surgical site as is generally known in the art, for example by making an open, minimally-invasive or other incision in the skin and subdermal tissues to obtain access to the desired surgical site. In this description, spinal surgery will be described as a principal example of the use of the above-described embodiments. Once access to a vertebra has been obtained, the surgeon prepares a hole in the vertebra. Screw 20 is then introduced to the surgical site and threaded or otherwise inserted into the hole in the vertebra. A holding tool (not shown) with protrusions connected to screw 20 via indentations 90 can be used to hold and either begin to insert or completely insert screw 20 into a hole in the vertebra. It will be seen that if shaft 22 is self-tapping, then it will not be necessary to tap or otherwise thread the hole in the vertebra. Where a hook or other implant is employed, rather than a screw, shaft 22 (in the form of a hook blade or other structure) will be connected to the vertebra, as by hooking it around or otherwise in contact with a pedicle, process or other vertebral part.

When the anchor 20 is connected to a bone, a rod can be maneuvered to the surgical site, contoured as may be desired, and then inserted into channel 52 of receiving portion 24 via mouth 54. The rod is placed in receiving portion 24 until it is adjacent or in contact with seat portion 63 of internal piece 26. The rod may be pressed against surface 68 of internal piece 26, which will result in a camming action to push seat portion 63 of internal piece 26 relatively downward so that the rod becomes adjacent to internal surface 66 of seat portion 63. In that position, the rod and internal piece 26 are rotatable substantially in a plane with respect to receiving portion 24, for example substantially within a sagittal plane relative to the spine. Such rotation is substantially around the axis of post portion 64 of internal piece 26. Once the rod and internal piece 26 are in the desired position with respect to receiving portion 24, set screw 48 is threaded down through upper leg 40 of receiving portion 24 and into contact with the rod. Screw 48 forces the rod against seat portion 63 of internal piece 26, forcing external surface 67 of internal piece 26 against lower leg 42 of receiving portion 24, e.g. against one or more ridges 62. In an embodiment in which set screw 48 has a curved or conical bottom surface 49, such bottom surface 49 will tend to push the rod in a direction substantially toward intermediate portion 44 and/or lower leg 42 of receiving portion 24. In an embodiment in which set screw 48 has a pointed bottom surface 49, such point(s) may bite into the rod. The rod is then locked with respect to internal piece 26 and receiving portion 24, and internal piece 26 is locked with respect to receiving portion 24.

Additional screws 20 can be placed in adjacent or relatively distant bone tissue to connect to the same or additional rods. Further, other components, such as alternative screw or hook apparatus, clamps, connectors, or similar devices can be placed in connection with such rod(s) and such bone tissue(s). As may be desired by the surgeon or necessitated by the given trauma or other physical situation, bone growth materials, such as bone morphogenic protein (BMP), demineralized bone matrix (DBM), bone graft, or other substances may also be used in connection with parts of the structures described above so as to repair or correct the patient's physical situation.

Materials for set screw 48, internal piece 26, ridges 62 and/or the rod can be chosen so that some deformation or penetration of one part with respect to another may occur. For example, if set screw 48 is provided with one or more points or edges on a bottom surface (e.g. curved or conical surface 49), such points or edges (or the overall material of set screw 48) can be made of a harder material than the rod so that set screw 48 bites into the rod as set screw 48 is tightened to lock the rod within receiving portion 24. As another example, if internal piece 26 is of a softer material than ridges 62 of receiving portion 24, then ridges 62 may bite into external surface 67 of internal piece 26 on locking the construct.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

For example, the specific embodiment of screw 20 can be sized for placement at any level of the spine. Of course, it is understood that the relative size of the components of the assembly will be modified for the particular vertebra(e) to be instrumented. For example, components may be relatively larger for lumbar or sacral placement than those for cervical placement. Likewise, the relative dimensions of post portion 64 of internal piece 26 and area 60 of cavity 56, and/or the relative dimensions of the rod and receiving portion 24, can be chosen to permit greater or lesser degrees of angulation of the rod relative to receiving portion 24.

The components described above may be formed of stainless steel or other biocompatible materials, such as titanium, certain plastics or ceramics, and materials that permit bone ingrowth.

Further, while the embodiment discussed above concerns a bone screw, other bone fixation members can be adapted to implement the features disclosed herein. For instance, as noted above shaft 22 could be the blade of a vertebral hook rather than a threaded element.

It is also understood that while the preferred embodiment of the invention engages a bone screw to a rod, various longitudinal members are contemplated. For example, an elongated bar can be disposed within the channel of the receiving portion to be clamped between internal piece 26 and set screw 48. Such a rod or longitudinal member can be a part of a lateral connector or other piece used in orthopedic surgery. The present invention can be applied equally well to smooth rods or bars, or longitudinal members having various surface features, such as knurling or threading.

The entire disclosure of the U.S. patent application entitled "SIDE LOADING BONE ANCHOR" and filed on Dec. 1, 2004, is incorporated herein by reference.

What is claimed is:

1. An apparatus for attachment to a vertebra and a spinal rod, comprising:
    a bone anchor portion having a threaded shaft with a longitudinal axis and a neck, said threaded shaft having cancellous threads suited to connection to a vertebra;
    a substantially C-shaped receiving portion having a lower leg integrally connected to said neck of said bone anchor portion and an upper leg and an intermediate portion, said receiving portion having a channel substantially perpendicular to said axis into which a rod can be placed in said receiving portion, said channel having a mouth for introduction of said rod, said receiving portion further including an internally threaded aperture through said upper leg, said receiving portion further including an opening in said lower leg and said intermediate portion, said receiving portion further including at least one exterior imprint adapted for accommodating a holding tool;
    an internal piece connected to said receiving portion so that at least a portion of said internal piece is within said opening of said receiving portion, said internal piece having a post portion extending into said intermediate portion of said receiving portion, and a seat portion having a first end and a second end, said first end of said seat portion being attached to said post portion of said internal piece, said second end having a flat portion, said seat portion having a substantially cylindrical inner surface having an arc of up to about 120 degrees, and said post portion having a groove; and
    a ring member surrounding at least a portion of said post portion of said internal piece such that at least a portion of said ring member is within said groove, wherein said ring member is positioned so that said internal piece and said receiving portion are rotatable with respect to each other and so that said post portion of said internal piece and said ring member cannot be withdrawn from said opening of said receiving portion.

2. The apparatus of claim 1, wherein said opening of said receiving portion has a part that has substantially an hourglass shape.

3. The apparatus of claim 1, wherein said receiving portion includes at least one ridge adjacent said opening in said receiving portion and adjacent said seat portion of said internal piece.

4. The apparatus of claim 1, wherein said channel in said receiving portion is tapered from said mouth toward said intermediate portion.

5. The apparatus of claim 1, wherein said exterior imprint of said receiving portion includes at least one indentation for receiving a tool portion, said indentation having an entry portion, a holding portion with a substantially circular part, and a corner between said holding portion and said entry portion, whereby a tool portion may be inserted through said entry portion in one direction and into said holding portion in another direction.

6. The apparatus of claim 1, wherein an elongated member is within said channel and adjacent said seat portion of said internal piece, and further comprising a set screw threaded into said upper leg and against said elongated member whereby said elongated member, said internal piece, said receiving portion are locked together.

7. A side-loading bone anchor apparatus, comprising:
    a substantially C-shaped receiving portion having a lower leg, an upper leg and an intermediate portion, said receiving portion having a channel between said upper and lower legs and substantially perpendicular to said intermediate portion, said receiving portion further including a hollow in said lower leg and a hole in said intermediate portion;
    a bone anchor portion with a longitudinal axis connected to said lower leg of said receiving portion, said axis being substantially parallel to said intermediate portion;
    an internal piece including a post portion and a seat portion, said post portion being substantially linear and said seat portion having a substantially cylindrical inner surface, said seat portion having a first end and a second end, said first end of said seat portion being attached to said post portion, said second end having a flat portion that is non-parallel to said post portion, wherein said post portion of said internal piece is within said hole and does not extend beyond said intermediate portion and said seat portion is adjacent said hollow of said receiving portion, wherein said internal piece is rotatable about said post portion with respect to said receiving portion; and
    a set screw connected to said receiving portion,
    whereby said set screw and said seat portion of said internal piece are adapted to contact an elongated member positioned in said channel to lock the elongated member, said seat portion, and said receiving portion with respect to each other.

8. The apparatus of claim 7, wherein said receiving portion includes at least one ridge adjacent said hollow, said ridge adapted to contact said internal piece.

9. The apparatus of claim 8, wherein said ridge deforms said internal piece when said apparatus is locked.

10. The apparatus of claim 7, wherein said flat portion of said internal piece is angled so that when a rod contacts said flat portion as the rod is side-loaded into said receiving portion, said seat portion of said internal piece is pushed toward said hollow.

11. The apparatus of claim 7, wherein said flat portion of said internal piece and said inner surface of said internal piece meet in a ridge substantially perpendicular to said post portion.

12. The apparatus of claim 7, wherein said hole has at least a portion in an hour-glass shape.

13. The apparatus of claim 12, wherein said hour-glass portion of said hole has upper and lower surfaces that are curved.

14. The apparatus of claim 7, wherein said post portion includes substantially smooth flat sides and substantially smooth curved top and bottom surfaces.

15. The apparatus of claim 7, wherein said post portion includes a groove, said receiving portion includes a rim surrounding at least a portion of said hole, and further comprising a clip member at least partially within said groove and adjacent said rim.

16. The apparatus of claim 7, wherein a spinal rod is within said channel and adjacent said seat portion of said internal piece, and wherein said set screw is threaded into said upper leg and against said rod whereby said rod, said internal piece, said receiving portion are locked together.

17. The apparatus of claim 7, wherein said upper leg has an underside nonperpendicular to said intermediate portion.

18. The apparatus of claim 7, wherein said channel tapers toward said intermediate portion.

19. The apparatus of claim 18, wherein said flat portion of said internal piece defines in part said tapering channel.

20. An apparatus for attachment to a vertebra and a spinal rod, comprising:
a bone anchor portion having a threaded shaft with a longitudinal axis and a neck, said threaded shaft having a longitudinal axis and cancellous threads suited to connection to a vertebra;
a substantially C-shaped receiving portion having a lower leg integrally connected to said neck of said bone anchor portion and an upper leg and an intermediate portion, said receiving portion having a channel substantially perpendicular to said axis into which a rod can be placed in said receiving portion, said channel having a mouth for introduction of said rod, said receiving portion further including an internally threaded aperture through said upper leg, said receiving portion further including an opening in said lower leg and said intermediate portion, said receiving portion further including at least one exterior imprint adapted for accommodating a holding tool;
an internal piece connected to said receiving portion so that at least a portion of said internal piece is within said opening of said receiving portion, said internal piece having a post portion extending into said intermediate portion of said receiving portion, and a seat portion having a first end and a second end, said first end of said seat portion being attached to said post portion of said internal piece, said second end having a flat portion, said seat portion having a substantially cylindrical inner surface having an arc of up to about 120 degrees, and said post portion having a groove; and
a ring member surrounding at least a portion of said post portion of said internal piece such that at least a portion of said ring member is within said groove, wherein said ring member is positioned so that said internal piece and said receiving portion are rotatable with respect to each other and so that said post portion of said internal piece and said ring member cannot be withdrawn from said opening of said receiving portion;
wherein an elongated member is within said channel and adjacent said seat portion of said internal piece, and wherein no part of said internal piece is between said elongated member and said upper leg.

21. The apparatus of claim 20, wherein said opening of said receiving portion has a part that has substantially an hour-glass shape.

22. The apparatus of claim 20, wherein said channel in said receiving portion is tapered from said mouth toward said intermediate portion.

23. The apparatus of claim 20, further comprising a set screw threaded into said upper leg and against said elongated member whereby said elongated member, said internal piece, said receiving portion are locked together.

24. The apparatus of claim 20, wherein said flat portion of said internal piece is angled so that when a rod contacts said flat portion as the rod is side-loaded into said receiving member, said seat portion of said internal piece is pushed toward said hollow.

25. The apparatus of claim 20, wherein said post portion includes a groove, said receiving portion includes a rim surrounding at least a portion of said hole, and further comprising a clip member at least partially within said groove and adjacent said rim.

26. The apparatus of claim 1, wherein the maximum width of said channel substantially parallel to said longitudinal axis of said threaded shaft is the width of said mouth of said channel.

27. The apparatus of claim 1, wherein said lower leg includes a front portion and a back portion, said back portion leading to said intermediate portion of said receiving portion, wherein said neck is connected to said lower leg adjacent said front portion.

28. The apparatus of claim 1, wherein said inner surface of said seat portion includes a radius of curvature configured to substantially mate with the radius of curvature of the spinal rod received in the receiving portion.

29. The apparatus of claim 1, wherein said lower leg includes an inner surface partially defining said opening and said internal piece includes a lower surface facing said inner surface of said lower leg, wherein said internal piece is connected to said receiving portion such that when a rod is side-loaded into said receiving portion, said lower surface is pushed toward said inner surface to allow for the introduction of the rod.

30. The apparatus of claim 1, wherein said flat portion of said internal piece is angled so that when a rod contacts said flat portion as the rod is side-loaded into said receiving portion, said seat portion of said internal piece is pushed toward said opening in said lower leg.

31. The apparatus of claim 7, wherein said channel includes a mouth for introduction of an elongated member, and wherein the maximum width of said channel substantially parallel to said longitudinal axis of said bone anchor portion is the width of said mouth of said channel.

32. The apparatus of claim 7, wherein said lower leg includes a front portion and a back portion, said back portion leading to said intermediate portion of said receiving portion, wherein said bone anchor portion is connected to said lower leg adjacent said front portion.

33. The apparatus of claim 7, wherein said inner surface of said seat portion includes a radius of curvature configured to substantially mate with the radius of curvature of an elongated member received in the receiving portion.

34. The apparatus of claim 7, wherein said lower leg includes an inner surface partially defining said hollow and said internal piece includes a lower surface facing said inner surface of said lower leg, wherein said internal piece is connected to said receiving portion such that when an elongated member is side-loaded into said receiving portion, said lower surface is pushed further within said hollow toward said inner surface to allow for the introduction of the elongated member.

* * * * *